United States Patent [19]
Rydell

[11] Patent Number: 5,250,047
[45] Date of Patent: Oct. 5, 1993

[54] BIPOLAR LAPAROSCOPIC INSTRUMENT WITH REPLACEABLE ELECTRODE TIP ASSEMBLY

[75] Inventor: Mark A. Rydell, Golden Valley, Minn.

[73] Assignee: Everest Medical Corporation, Minneapolis, Minn.

[21] Appl. No.: 780,045

[22] Filed: Oct. 21, 1991

[51] Int. Cl.⁵ .............................................. A61B 17/39
[52] U.S. Cl. ............................................. 606/48; 606/50
[58] Field of Search .................... 606/45, 46, 48–52

[56] References Cited

U.S. PATENT DOCUMENTS

| | | | |
|---|---|---|---|
| 1,814,791 | 7/1931 | Ende | 606/50 |
| 3,746,814 | 7/1973 | Lackey et al. | |
| 3,920,021 | 11/1975 | Hiltébrandt | 606/50 |
| 4,311,145 | 1/1982 | Esty et al. | 606/51 X |
| 4,418,692 | 12/1983 | Guay | |
| 4,657,016 | 4/1987 | Garito et al. | |
| 4,688,569 | 8/1987 | Rabinowitz | |

FOREIGN PATENT DOCUMENTS

| | | |
|---|---|---|
| 2262209 | 7/1973 | Fed. Rep. of Germany. |
| 2324658 | 12/1974 | Fed. Rep. of Germany. |
| 0256648 | 5/1988 | Fed. Rep. of Germany ........ 606/46 |

Primary Examiner—Lee S. Cohen
Attorney, Agent, or Firm—Haugen and Nikolai

[57] ABSTRACT

An electrosurgical instrument for use in endoscopic procedures features an electrode assembly which can be readily connected and disconnected from the remaining body of the instrument to allow a replacement electrode assembly to be substituted. The instrument comprises an elongated rigid tube having a handle on the proximal end, the handle including a spring-loaded plunger which is connected by a push rod to a stem member disposed in the lumen of the tube near its distal end. The electrode assembly is designed to mate with the stem and when the plunger is actuated to extend the stem beyond the distal end of the tube, the electrode assembly may be installed. Retraction of the stem within the lumen of the tube serves to hold the electrode assembly in place.

4 Claims, 1 Drawing Sheet

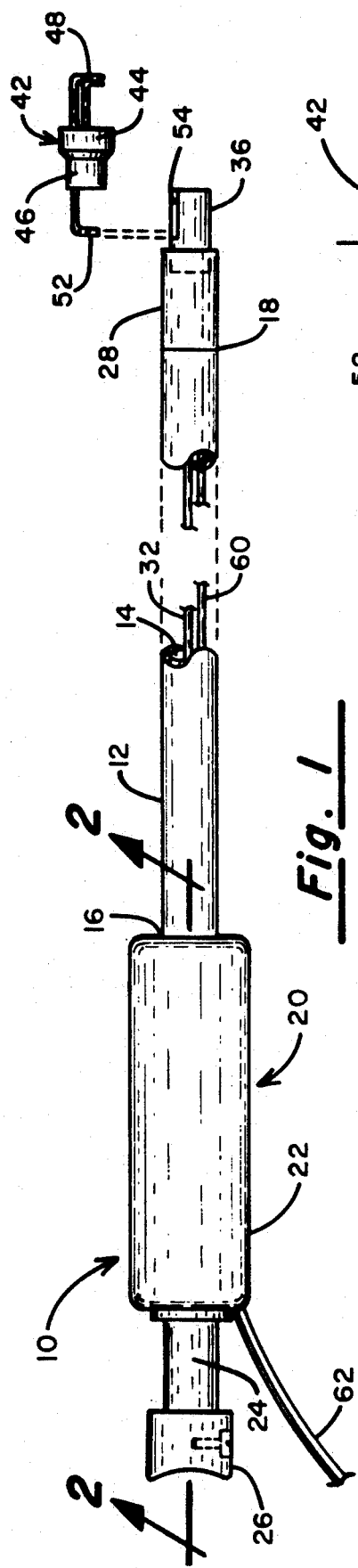
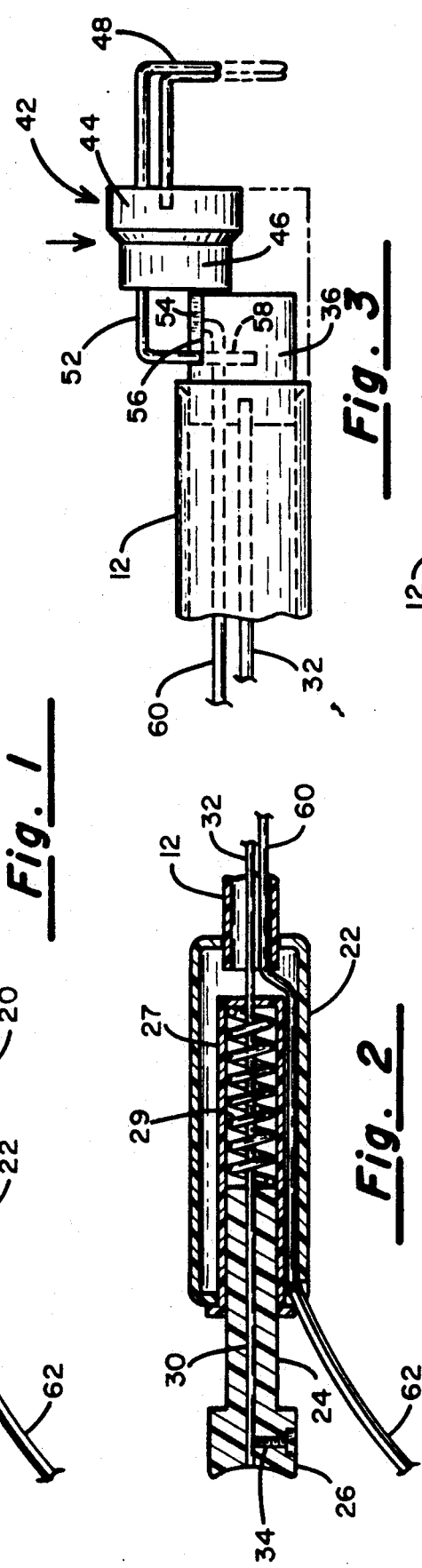
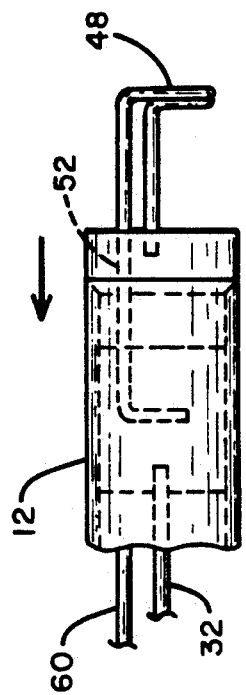
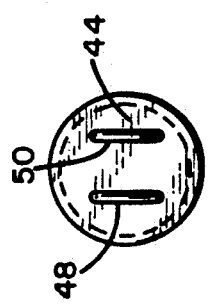

BIPOLAR LAPAROSCOPIC INSTRUMENT WITH REPLACEABLE ELECTRODE TIP ASSEMBLY

BACKGROUND OF THE INVENTION

I. Field of the Invention

This invention relates generally to electrosurgical instruments, and more particularly to an electrosurgical instrument for cutting and coagulating when performing minimally invasive surgery via an endoscope and incorporating means for quickly and easily removing and replacing the electrode structure. As used herein, the term "endoscope" is intended to genericly cover and include more specific instruments, including, for example, laparoscopes, cystoscopes, arthroscopes, hysteroscopes and the like.

II. Discussion of the Prior Art

With the advent of improved equipment for viewing a surgical site internal to the body using optical fibers routed through small diameter tubes, such as endoscopes, improved surgical procedures have been devised in which microminiaturized instruments may be routed through cannulae or a working lumen in the endoscope itself for surgically removing or repairing diseased or damaged organs without the need for making large incisions to expose the area allowing the surgeon to view the surgical site. For example, it is now possible in many cases to remove a defective gallbladder without making a large incision through the abdominal wall. Instead, in a procedure called laparoscopic cholecystectomy, a series of tiny puncture wounds are made through the abdomen and a laparoscope, for viewing the internal surgical site, and other tubes for passing cutting and/or grasping instruments are inserted. By appropriately manipulating the instruments within their respective tubes, the gallbladder can be excised from surrounding tissue, emptied of its contents and then retracted back through the small tube. Using this laparoscopic procedure, a patient who might otherwise be hospitalized for a week or more and who may have to undergo a month of recuperation before returning to normal activities can leave the hospital the next day and return to work within only a few days.

The laparoscopic cholecystectomy procedure alluded to above is only one of a series of surgical procedures that have been made possible using endoscopes and the like. In applicant's copending application Ser. No. 07/516,740, now U.S. Pat. No. 5,071,419, filed Apr. 30, 1990, and entitled "PERCUTANEOUS LAPAROSCOPIC CHOLECYSTECTOMY INSTRUMENT", there is described an electrosurgical instrument especially designed for carrying out minimally invasive procedures, via an endoscope-type device. It comprises an elongated tube having a pair of spaced-apart hook-shaped electrodes permanently affixed to the distal end thereof and a hub or handle member affixed to its proximal end. Electrical conductors enter the handle and pass through the lumen of the elongated tube and are electrically connected to the hook-shaped electrodes. Means are also provided for allowing irrigation and aspiration of the surgical site.

During a given surgical procedure, it may become necessary to substitute different electrodes, either because the existing electrodes become fouled with charred tissue and blood rendering them ineffective for cutting or because electrodes of differing shape configuration may more readily be used than the existing ones to surmount a particular obstacle or to achieve a more desired cutting pattern.

Prior to the present invention, electrosurgical instruments for endoscopic procedures all have had monopolar or bipolar electrodes permanently affixed to the distal end of the instrument. Hence, in the event that the electrosurgical electrodes became fouled to the point where they cannot be wiped clean, it has been necessary to remove and discard the entire instrument, thus adding to the cost of the procedure.

OBJECTS

It is accordingly a principal object of the present invention to provide an improved electrosurgical instrument for use in carrying out endoscopic surgical procedures.

Another object of the invention is to provide an improved electrosurgical instrument having removable and replaceable electrodes attachable to the distal end thereof.

Another object of the invention is to provide an improved electrosurgical instrument in which the electrode structures used for effecting RF cutting and coagulation can be rapidly and easily removed from the distal end of the instrument and replaced with clean electrodes or electrodes having a differing shape configuration.

SUMMARY OF THE INVENTION

In accordance with the present invention, the electrosurgical instrument for use in endoscopic procedures comprises an elongated, rigid tube having a handle affixed to the proximal end thereof, the handle including a spring-biased, manually-operable plunger. A stem member which is dimensioned to slide longitudinally within the lumen of the rigid tube is connected to the plunger by means of a push rod and, when the plunger is depressed, the stem member is made to extend outward beyond the distal end of the rigid tube. A replaceable electrode assembly including an insulating support to which one or more electrodes are mounted is adapted to be joined to the stem member when it is made to extend beyond the distal end of the rigid tube. Once the support member is coupled to the stem and the stem is retracted into the lumen of the rigid tube, the replaceable electrode assembly is firmly coupled, both mechanically and electrically to the instrument. When it is desired to remove and substitute a new electrode assembly, the surgeon need only depress the plunger to the point where the stem member extends beyond the distal end of the rigid tube, allowing the electrode assembly to be removed and replaced.

DESCRIPTION OF THE DRAWINGS

The foregoing features, objects and advantages of the invention will become apparent to those skilled in the art from the following detailed description of a preferred embodiment, especially when considered in conjunction with the accompanying drawings in which like numerals in the several views refer to corresponding parts.

FIG. 1 is a side elevation of the electrosurgical instrument in accordance with the present invention;

FIG. 2 is a partial cross-section of the handle portion of the instrument of FIG. 1;

FIG. 3 is an enlarged partial view of the distal end portion of the instrument of FIG. 1 showing the manner in which the electrode structure can be removed and replaced;

FIG. 4 is an enlarged partial view of the distal end portion of the instrument of FIG. 1; and FIG. 5 is an end view of the electrosurgical instrument of FIG. 1.

DESCRIPTION OF THE PREFERRED EMBODIMENT

Referring first to FIG. 1, there is indicated generally by numeral 10 an electrosurgical instrument especially designed for use in carrying out endoscopic procedures. It is seen to include a generally rigid, elongated tube 12 which may be formed from a suitable plastic or from metal, preferably stainless steel. The tube 12 has a lumen 14 running the full length thereof from its proximal end 16 to its distal end 18. Affixed to the proximal end of the tube 12 is a handle member indicated generally by numeral 20 and projecting from the proximal end of the body 22 of the handle is a spring-loaded plunger 24 having a thumb-rest 26 affixed to its proximal end. As seen in the cross-sectional view of FIG. 2, the handle contains a molded plastic cage 27 into which a compression spring 29 is fitted. The spring abuts the plunger 24, biasing it in the proximal direction.

When a metal such as stainless steel is used for fabricating the tube 12, it is desirable to affix to the distal end 18 of that metal tube a short tubular stub 28 which is made from an electrically insulating material, such as plastic or ceramic. If the entirety of the tube 12 is formed from plastic, however, it becomes unnecessary to append an insulating stub as at 28 to the distal end of that plastic tube.

With continued reference to FIGS. 1 and 2, extending longitudinally through the thumb pad 26, the plunger rod 24 and the handle body 22 is a longitudinal bore 30 into which is fitted a push rod 32. It is fastened at its proximal end to the plunger assembly by a set screw 34. Those skilled in the art can appreciate, however, that other means are available for securing the push wire 30 to the plunger and that a set screw is intended to be illustrative only.

The push rod 32 also extends longitudinally through the lumen 14 of the elongated rigid tube 12 toward the distal end thereof where it is affixed to a cylindrical stem 36 that loosely fits within the lumen of the tube 12 or the stub 28, as the case may be. Hence, when a force is applied in the distal direction to the thumb rest 26, the plunger 34 compresses the spring 29 within its cage 27. This movement causes the stem member 36 to be extended distally beyond the end of the stub 18 (FIG. 1). When the force is removed, the spring 29 is allowed to expand and move the plunger 34 in the proximal direction and because the push rod 32 is fastened thereto and to the stem 36, the stem 36 retracts fully into the lumen of the tube 12 or the stub 28 when a metal is used for tube 12.

Referring now to FIGS. 1, 3, 4 and 5, the removable electrode assembly is identified generally by numeral 42 and includes an insulating stepped-diameter plug 44 whose outside diameter at its distal end is equal to the outside diameter of the tube 12 and/or the stub 28. The plug 44 has an integrally formed and proximally extending section 46 of a reduced diameter, that diameter being generally equal to the inside diameter of the tube 12 and/or the stub 28. A pair of electrodes 48 and 50 are fitted into bores formed lengthwise through the member 44 and, as indicated in FIG. 5, are generally parallel and spaced apart from one another by a predetermined gap. Each of the electrodes 48 and 50 terminates in a proximal L-shaped terminal segment 52.

Assuming a bipolar instrument is involved, the stem 36 has a pair of notches or grooves formed inwardly from a peripheral surface thereof, only one of the grooves being visible and is identified by numeral 54 in FIG. 3. Fitted into the bottom of each of the grooves 54 is an electrical contact pad 56 which extends for a short predetermined length from a radially-extending bore 58 to the distal end of the stem 36. These contact pads are connected by electrical conductors 60 through the lumen of the tube 12 and back through the handle body 22 where they come together to form an electrical cord 62 leading to an electrical surgical generator (not shown).

As can best be seen in FIG. 3, the L-shaped terminal 52 of the electrodes 48 and 50 are designed to fit into the radial bores 58 and, when fully inserted, a portion of the terminal 52 firmly engages the electrical contact pad 56. When the pressure is released from the thumb rest 26, the stem 36 retracts fully into the lumen of either the tube 12 or the stub 28 and, in doing so, the terminals 52 are held firmly within the grooves 54 and against their respective contact pads 56, thus establishing an electrical connection to the electrodes 48 and 50. This arrangement is best shown in FIG. 4.

Following a period of use of the electrosurgical instrument, it may no longer be possible to simply wipe burnt tissue debris from the electrodes 48 and 50, thus necessitating replacement of the electrode assembly 42. To accomplish this, the plunger 24 is depressed by applying a force to the thumb rest member 26. This compresses the spring 29 and, by virtue of the push rod 32, pushes the stem 36 outward beyond the distal end of the tube 12 or the stub 28. Once the stem 36 is so extended to expose the terminals 52, the electrode assembly 42 can easily be lifted free of the distal end of the stem by pulling the terminals 52 free of their respective bores 58. A new terminal assembly can then be attached to the distal end of the instrument by having its terminals 52 inserted into the bores 58 and then releasing the pressure on the plunger 24, such that the spring 29 urges the push rod 32 in the proximal direction carrying the stem member 36 and the electrode assembly 42 with it. When the stem 36 is retracted within the I.D. of the tube 12 or the stem 28 the terminal portion 52 of the electrodes is held in firm contact with the contact pads 56 formed on the stem and because of the overlapping of the tube 12 or stem 28 with the terminal portion of the electrode assembly, the electrode assembly is firmly held in place.

As mentioned in the introductory portion of this specification, the electrode assembly 42 may be not only replaced because it has been fouled by the buildup of tissue debris, but it may also be desirable to substitute electrodes having a different shape configuration so that the surgical procedure can better be accommodated.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. An electrosurgical instrument for use in endoscopic procedures, comprising:
   (a) an elongated, rigid tube having a proximal end, a distal end and a lumen extending therebetween;
   (b) a handle affixed to the proximal end of the tube;
   (c) a stem member disposed within the lumen of the tube and having a proximal end, a distal end and an outer dimension corresponding to the inside dimension of said lumen whereby the stem member can slide longitudinally within the lumen, said stem member having first and second electrical contact pads and first and second radial bores,;
   (d) means disposed in the handle coupled to the stem member for imparting longitudinal reciprocal movement to the stem member;
   (e) a replaceable electrode assembly releasably secured to the distal end of the stem member and extending distally from the distal end of the tube, wherein the assembly includes:
      (i) an insulating support member having at least a portion thereof dimensioned to closely fit within the distal end of the lumen of the tube; and
      (ii) a pair of bipolar electrodes extending outwardly from the support member, said electrodes having electrical terminals which are L-shaped wire segments whereby a portion of each segment engages one electrical contact pad of the stem member and a portion of each segment resides within one radial bore of the stem member; and
   (f) means for coupling an electrosurgical generator to the electrode assembly.

2. An electrosurgical instrument as claimed in claim 1 wherein the L-shaped wire segments are retained in said radial bores when the stem member is retracted into the lumen, and said wire segments are removable from said radial bores when the stem member is moved longitudinally beyond the distal end of said tube.

3. An electrosurgical instrument as claimed in claim 1 wherein the stem member has a pair of grooves which extend longitudinally from the radial bores to the distal end of the stem member and within which are disposed the electrical contact pads.

4. An electrosurgical instrument as claimed in claim 1, 2 or 3 wherein the means disposed in the handle comprise:
   (a) a manually operable, spring-biased plunger slidingly received in said handle; and
   (b) a push rod coupling said spring-biased plunger to said stem member.

* * * * *